(12) United States Patent
Pirovano et al.

(10) Patent No.: US 6,414,210 B1
(45) Date of Patent: Jul. 2, 2002

(54) PROCESS FOR THE SEPARATION OF LIGHT OLEFINS FROM PARAFFINS

(75) Inventors: Carmen Pirovano, San Donato Milanese; Domenico Sanfilippo, Paullo; Francesco Saviano, Segrate; Laura Piovesan, Venezia, all of (IT)

(73) Assignee: Snamprogetti S.p.A., San Donato Milanese (IT)

( * ) Notice: Subject to any disclaimer, the term of this patent is extended or adjusted under 35 U.S.C. 154(b) by 0 days.

(21) Appl. No.: 09/619,319

(22) Filed: Jul. 18, 2000

(30) Foreign Application Priority Data

Jul. 22, 1999 (IT) .......................... MI99A1613

(51) Int. Cl.[7] .......................... C07C 7/10; C07C 7/152; C07C 7/00
(52) U.S. Cl. .................. 585/843; 585/850; 585/805
(58) Field of Search .................. 585/809, 843, 585/850

(56) References Cited

U.S. PATENT DOCUMENTS

| | | | |
|---|---|---|---|
| 3,189,658 A | | 6/1965 | Quinn .......................... 585/844 |
| 3,758,605 A | * | 9/1973 | Hughes et al. .............. 206/677 |
| 5,859,304 A | * | 1/1999 | Barchas et al. ............. 585/809 |

* cited by examiner

*Primary Examiner*—Walter D. Griffin
*Assistant Examiner*—Tam Nguyen
(74) *Attorney, Agent, or Firm*—Oblon, Spivak, McClelland, Maier & Neustadt, P.C.

(57) ABSTRACT

Process for the separation of light olefins from paraffins contained in mixtures, optionally also containing hydrogen, comprising bringing said mixtures into contact with an aqueous solution of one or more compounds of silver, preferably silver nitrate, and one or more ferric compounds, preferably ferric nitrate.

13 Claims, 4 Drawing Sheets

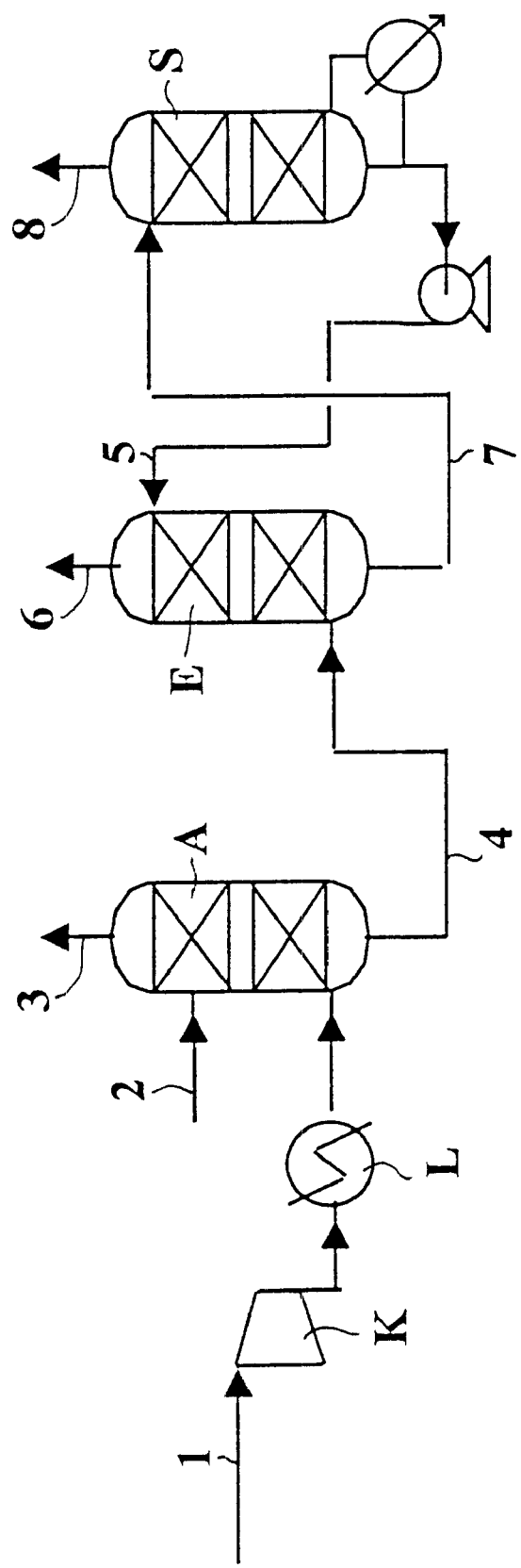

PROCESS FOR THE SEPARATION OF LIGHT OLEFINS FROM PARAFFINS

Figure 1:
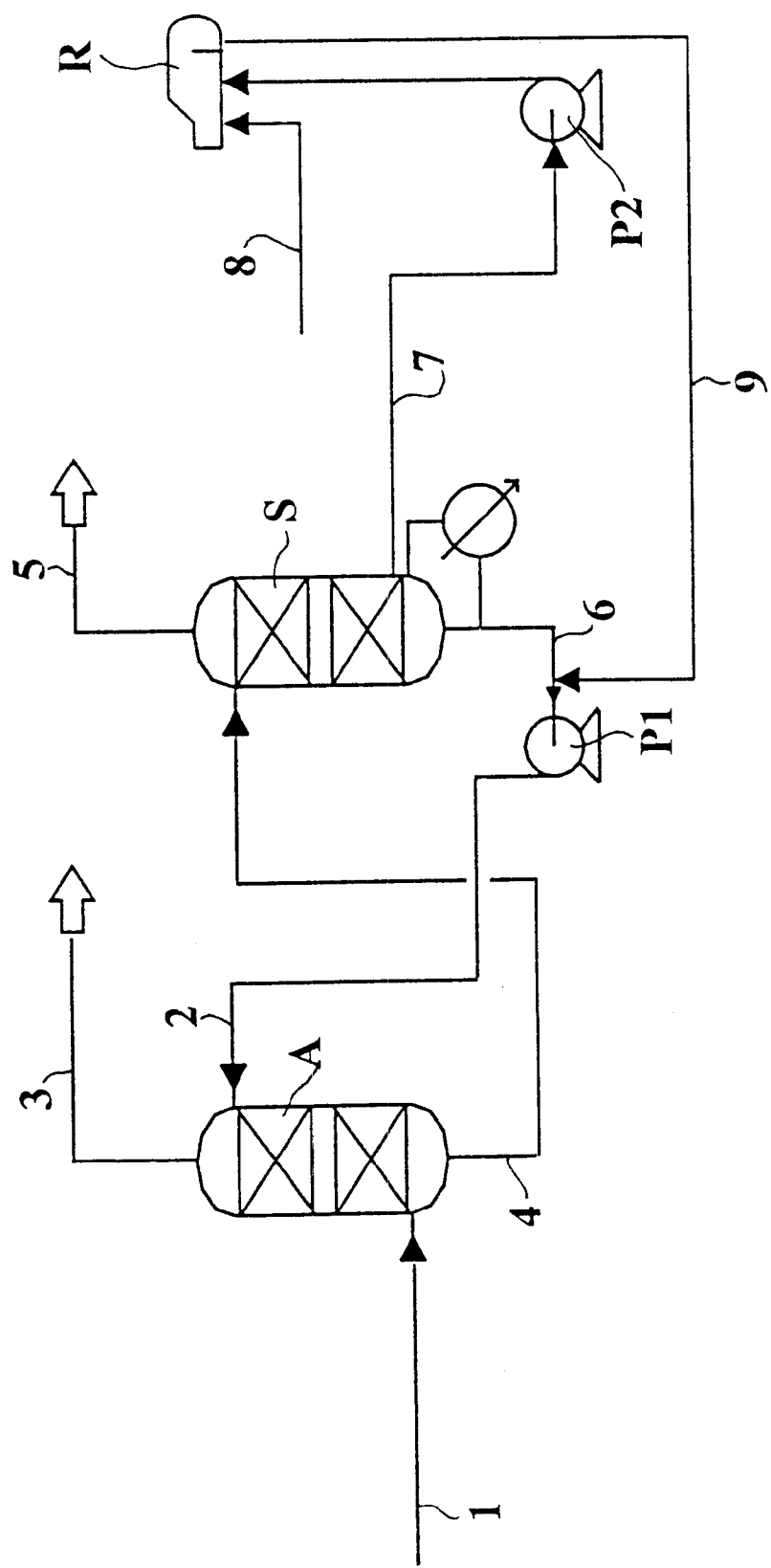

The present invention relates to a process for the separation of light olefins, having from 2 to 5 carbon atoms, from paraffins. In particular, light olefins and paraffins may be present in streams coming from ethylene/propylene production plants, either traditional (steam cracking of gaseous charges, secondary streams from FCC for the production of fuels) or innovative (catalytic dehydrogenation of ethane/propane).

The separation process of olefins by the reversible formation of π complexes with metal salts, and, in particular, with copper(I) and silver(I) salts, has been known for a long time: some applications go back to the forties', whereas the separation of ethylene with silver fluoborate was effected more or less in the sixties'. Since then various industrial applications have been developed, which have mainly privileged the use of solutions of copper salts (e.g. CO separation).

One of the reasons for which the use of solutions of $Ag^+$ was not successful in the field of the separation of olefins via absorption, although silver solutions have a high transporting capacity of olefins (at least double with respect to solutions of Cu(I) with an equal concentration), is the instability of the solution, which is particularly evident in the presence of a reducing environment. In fact, in reducing atmospheres, the $Ag^+$ ion undergoes a reduction reaction to metal Ag: $Ag^+ + e^- \rightarrow Ag$.

The metal silver generated, separates from the solution in the form of a particulate reducing the olefin transporting capacity of the absorption solution.

The solution which is normally proposed for overcoming the instability of silver solutions, is the addition of hydrogen peroxide which, in an acid environment, is capable of oxidizing (re-dissolving) metal Ag to $Ag^+$ ion, re-establishing the initial transporting capacity of the solution.

The use of $H_2O_2$ is not without disadvantages, among which the most important is the cost of the reagent, as well as its thermal instability.

Processes for the recovery of olefins based on the formation of n complexes with metals which have been commercialized, are limited to very few examples ("Separation and Purification Technology", N. N. Li, J. M. Calo-M. Dekker, Inc., 1992): among others, the separation of ethylene with a solution of copper nitrate/ethanolamine, which, initiated during the second world war, only operated for a short period.

In the fifties', Hoechst developed a process for the recovery of ethylene via absorption, using a concentrated aqueous solution of Ag fluoborate to fluoboric acid (U.S. Pat. No. 2,913,505). This process passed through a pilot-plant level and demonstrative steps, without reaching final commercialization, due to an unsatisfactory economic result.

The activity effected by Hoechst illustrated the main problems connected with the use of a silver solution, which are the formation of Ag acetylides (explosive in the dry state), the reduction of the $Ag^+$ ion with destabilizing effects of the process solution and the considerably corrosive nature of fluoborate, which obliges the use of valuable, and therefore costly, metal materials for the plant construction.

Union Carbide experimented on a pilot-plant level, the recovery of ethylene with an aqueous solution of $Ag^+$ nitrate, stabilizing the solution by the use of hydrogen peroxide and nitric acid. Silver permanganate is also added to the solution to oxidize the possible acetylene contained in the stream to be treated.

In addition to these, other processes have also been proposed which do not specifically refer to ethylene, but more generally to the separation of olefins from paraffins. These include the use of both aqueous and non-aqueous solvents to which salts, various types of acids have been added (U.S. Pat. No. 3,347,948; U.S. Pat. No. 4,132,744; U.S. Pat. No. 2,449,793; U.S. Pat. No. 3,189,658), or are directed towards the use of alternative methods for improving the contact between solute and solvent, such as liquid/liquid extraction or functionalized membranes with $Ag^+$ (U.S. Pat. No. 3,758,603; U.S. Pat. No. 3,758,605; U.S. Pat. No. 3,770,842; U.S. Pat. No. 3,844,735; U.S. Pat. No. 3,801,664).

The traditional separation process scheme essentially comprises two steps: an absorption step and a stripping step.

The stream containing light olefins and paraffins is fed to an absorption column in which the olefins are absorbed by a particular absorbent (for example $AgNO_3 + H_2O_2$). A stream containing the paraffins and hydrogen leaves the head of this column and is sent to a separation step, whereas a stream consisting of the absorbent and olefins leaves the bottom and is, in turn, fed to a stripping column to separate the olefins from the absorbent which is recycled to the absorption column.

It has been surprisingly found that by adding a ferric compound ($Fe^{3+}$) to the absorbing solution consisting of a silver salt, instead of hydrogen peroxide as stabilizer of the silver solution, in a reducing environment, the disadvantages relating to the use of hydrogen peroxide are eliminated.

It has been observed that in a reducing atmosphere the reaction of the ferric ion to ferrous ion $$Fe^{3+} + e^- \rightarrow Fe^{2+}$$

becomes prevalent with respect to the reduction reaction of $Ag^+$; in this way the concentration of silver ions remains unaltered as do the transporting properties of the solution.

The advantage of the use of ferric salts particularly lies in the fact that the ferrous ions generated by the reduction reaction can be re-oxidized to ferric ions in the presence of air; consequently by providing an air-insufflation operation downstream of the desorption column, the absorption/desorption solution can be regenerated before entering the absorber.

The presence of ferric salts, moreover, gives the solution stability properties even at high temperatures so that the stripper can operate under conditions close to atmospheric conditions with a clear gain with respect to the overall economy of the processes so far proposed (Hoechst and Union Carbide) which use the stripper at sub-atmospheric pressure.

The process of the present invention for the separation of light olefins from paraffins contained in mixtures, optionally also containing hydrogen, essentially comprises bringing these mixtures in contact with an aqueous solution of one or more silver compounds, preferably a silver salt, more preferably silver nitrate, and one or more ferric compounds, preferably a ferric salt, more preferably ferric nitrate.

In the aqueous solution, the silver compound is in a concentration preferably ranging from 0.1 to 6 M, more preferably from 1 to 3 m, whereas the ferric compound is in a concentration preferably ranging from 0.1 to 4 M, more preferably from 0.5 to 2 M.

More specifically, the process can be carried out using various types of schemes which are described hereunder.

One process, with a scheme analogous to the traditional ones, essentially comprises two steps:

subjecting the mixture of light olefins and paraffins to absorption, whereby the light olefins are absorbed by an absorbent consisting of the aqueous solution of one or more compounds of silver and one or more ferric compounds described above, obtaining a stream containing paraffins and a stream containing the absorbent and light olefins absorbed;

subjecting the stream containing the absorbent and the light olefins absorbed to a stripping, whereby the light olefins absorbed are separated from the absorbent, which is recycled to the absorption step.

In the absorption step, it is preferable to operate at temperatures ranging from 30° C. to 50° C. and at pressures ranging from 7 to 50 atm., whereas in the stripping step, it is preferable to operate at temperatures ranging from 60° C. to 120° C. and at pressures ranging from 0.2 to 2 atm.

An illustrative scheme of the two-step process for the separation of light olefins from paraffins is provided in FIG. 1.

The stream containing light olefins and paraffins (1) is fed to an absorption column (A) in which the olefins are absorbed by the absorbing solution (2) consisting of one or more silver salts and one or more ferric salts. A stream (3) containing paraffins leaves the head of this column, and is sent to subsequent processing operations, and a stream (4) consisting of the absorbent and olefins leaves the bottom, and is, in turn, fed to a stripping column (S) to separate the olefins (5) from the absorbent (6). A part of the absorbent solution (7) is removed laterally from the stripper and is sent, by means of the pump (P2), to a Reclaimer (R) into which air (8) is insufflated in a quantity necessary for re-oxidizing that part of ferrous ions ($Fe^{2+}$) produced by the reducing action of the hydrogen to ferric ions ($Fe^{3+}$). The re-oxidized solution (9) and the bottom stream of the stripper (6) are recycled (2) by means of the pump (P1) to the absorption column (A).

A second process, in alternative to the first one, can be essentially carried out by means of the following two steps:

subjecting the mixture of light olefins and paraffins, after being at least partially liquefied, to absorption, whereby the light olefins are absorbed by an absorbent consisting of the aqueous solution of one or more silver compounds and one or more ferric compounds described above, obtaining at the head, a stream containing the paraffins and possible inert products, which is sent to a subsequent fractionation step, and at the bottom, a stream containing the absorbent and light olefins absorbed;

subjecting the stream containing the absorbent and light olefins absorbed to stripping, whereby the light olefins absorbed are separated from the absorbent, which is recycled to the absorption step.

The operating conditions of the process steps substantially correspond to the temperature and pressure ranges specified for the process described above.

Figure 2:
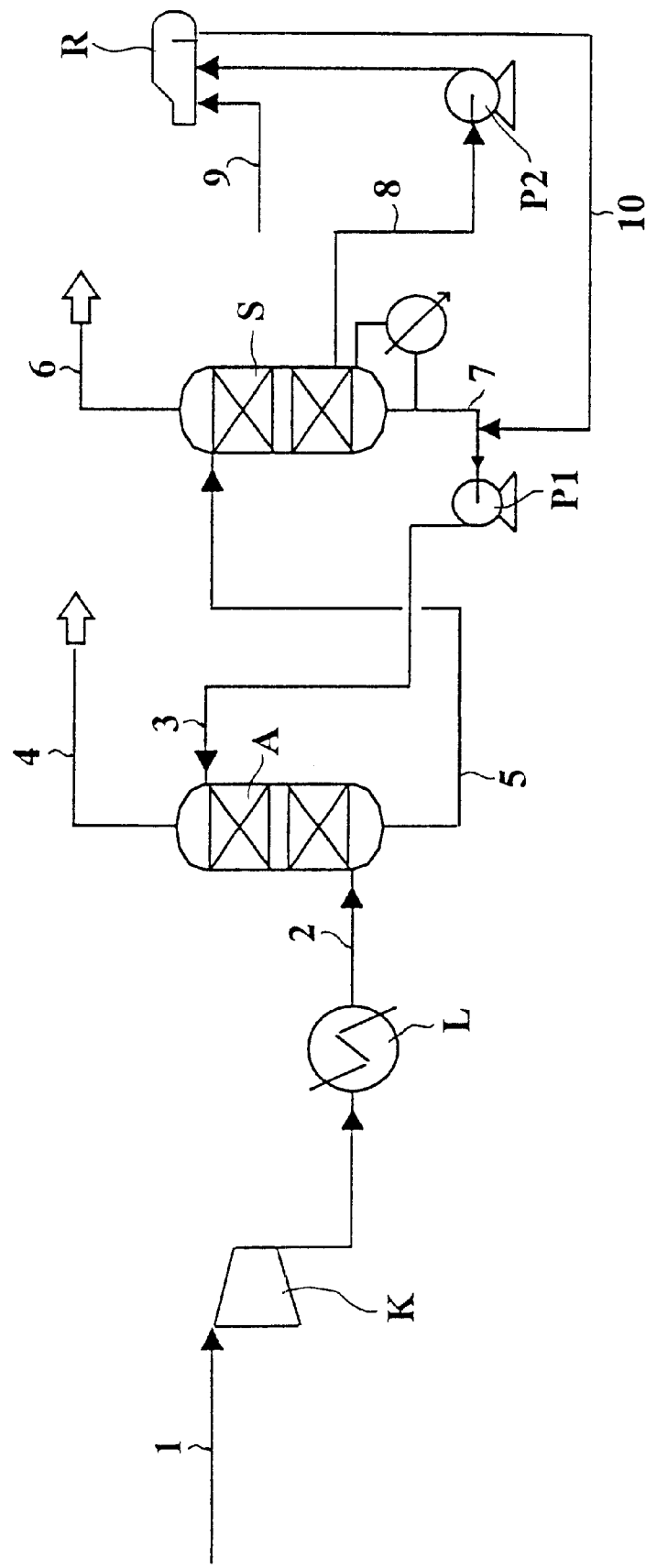

A general illustrative scheme of this alternative separation process is provided in FIG. 2.

The stream containing light olefins and paraffins (1), after being compressed in (K) and at least partially liquefied in (L), is fed (2) to an absorption column (A) in which the olefins are absorbed by the absorbent solution (3) consisting of one or more silver salts and one or more ferric salts. A stream (4) containing paraffins and inert products leaves the head of this column, and is sent to a subsequent separation step, whereas a stream (5), consisting of the absorbent and olefins, leaves the bottom and, in turn, is fed to a stripping column (S) to separate the olefins (6) from the absorbent (7). A part of the absorbent solution (8) is removed laterally from the stripper and sent, by means of the pump (P2), to a Reclaimer (R) into which air (9) is insufflated in a quantity necessary for re-oxidizing that part of ferrous ions ($Fe^{2+}$), produced by the reducing action of the hydrogen, to ferric ions ($Fe^{3+}$). The re-oxidized solution (10) and the bottom stream of the stripper (7) are recycled (3) by means of the pump (P1) to the absorption column (A).

A third alternative process, which, regardless of the absorbent solution used, solves the problem which arises when high concentrations of hydrogen are present in the mixtures, can be used.

This alternative process proposed differs in that the olefin/paraffin separation is carried out in a liquid-liquid extractor, after separation of the hydrogen and other possible inert products by absorption of the fraction of olefins and paraffins in a suitable hydrocarbon.

The process, which forms another object of the present invention, for the separation of light olefins from paraffins contained in mixtures containing hydrogen and/or other inert products ($N_2$, CO, etc.) is characterized in that it comprises the following steps:

subjecting the mixture to a separation by absorption in a suitable hydrocarbon in order to separate the hydrogen and/or other inert products from the hydrocarbons contained therein;

subjecting the mixture separated from the hydrogen and/or other inert products to a liquid/liquid extraction using a suitable extracting agent, obtaining a stream containing the paraffins and hydrocarbon absorbent and a stream containing the light olefins and extracting agent;

subjecting the stream containing the paraffins and hydrocarbon absorbent to a regeneration to obtain a stream essentially containing said hydrocarbon which is recycled to the separation step and a stream essentially containing paraffins;

subjecting the stream containing light olefins and extracting agent to regeneration to obtain a stream essentially containing the extracting agent which is recycled to the liquid-liquid extraction step and a stream essentially containing light olefins.

The separation step of hydrogen from the hydrocarbons contained in the mixture can be effected in an absorption column preferably operating at temperatures ranging from 30° C. to 50° C. and at pressures ranging from 7 to 50 atm.

The hydrocarbon absorbent used in this step can be selected from those having, at atmospheric pressure, a boiling point ranging from 30 to 220° C. The hydrocarbon absorbents preferably used are those having from 3 to 12 carbon atoms, in particular naphtha and propane, alone or mixed with each other.

The extraction step can be carried out in a liquid/liquid extraction column preferably operating at temperatures ranging from 30° C. to 70° C. and at pressures ranging from 7 to 50 atm.

The extracting agent can be selected from the same aqueous solutions of one or more compounds of silver and one or more ferric compounds described above or any solution that reversibly complexes the olefins such as, for example, cupro-ammonia solutions, if the stream fed does not contain high quantities of CO.

The regeneration step of the hydrocarbon absorbent can be effected in a stripping column preferably operating at temperatures ranging from 30° C. to 230° C. and at pressures ranging from 0.5 to 2 atm.

The regeneration step of the extracting agent can be carried out in a stripping column, preferably operating at temperatures ranging from 60° C. to 120° C. and at pressures ranging from 0.2 to 2 atm. If the extracting agent is a solution containing ferric salts, a reclaimer is necessary, as indicated in schemes 1 and 2, in which the re-oxidation operation of the ferrous ions, obtained by the action of hydrogen, to ferric ions, is effected.

A general illustrative scheme of the separation process described above is provided in FIG. 3.

The charge (1) is fed to the absorption column (A) into which a hydrocarbon absorbent (2), for example naphtha, is introduced. A gas stream (3) containing hydrogen leaves the head of the absorption column (A), whereas a liquid stream (4), containing the heavy hydrocarbon absorbent with the absorbed compounds (paraffins and olefins), is obtained from the bottom and is fed to the lower part of an extraction column (E). A liquid stream (6) essentially containing the hydrocarbon absorbent and paraffins is obtained at the head, with the use of an extraction solvent (5) fed to the upper part of the extraction column (E), and a liquid stream (7) essentially containing the extracting solvent and olefins, from the bottom.

The stream (7) is sent to a regeneration column (S) of the solvent, from which olefins (8) are obtained at the head and the regenerated extracting solvent (5) at the bottom, which is recycled to the extraction column (E).

The liquid stream (6) is, in turn, fed to a regeneration column of the absorbent (R) obtaining paraffins (9) at the head and the regenerated absorbent (2) at the bottom, which is recycled to the absorption column (A).

A fourth alternative process, which, regardless of the absorbing solution used, solves the problem arising when high concentrations of hydrogen are present in the mixtures to be separated and also allows the regeneration apparatus of the hydrocarbon absorbent to be eliminated, can be adopted.

The process, a further object of the present invention, for the separation of light olefins from paraffins contained in mixtures also containing hydrogen and/or other inert products ($N_2$, CO, etc.) is characterized in that it comprises the following steps:

subjecting the mixture of light olefins and paraffins, after being at least partially liquefied, to absorption, using a hydrocarbon identical to the paraffinic hydrocarbon contained in the mixture in a greater quantity, obtaining inert products and/or hydrogen at the head and a stream containing olefins and paraffins also comprising the hydrocarbon absorbent, at the bottom;

subjecting the bottom stream to liquid-liquid extraction by means of a suitable extracting agent, obtaining a stream essentially containing paraffins also comprising the hydrocarbon absorbent, at the head, and a stream substantially containing olefins and the extracting agent, at the bottom;

subjecting the stream containing olefins and the extracting agent to stripping, whereby the olefins are separated from the extracting agent, which is recycled to the liquid-liquid extraction step.

The extracting agent can be selected from the same aqueous solutions of one or more compounds of silver and one or more ferric compounds described above or any solution which reversibly complexes the olefins such as, for example, cupro-ammonia solutions.

The operating conditions of the process steps enter within the temperature and pressure ranges specified for the process previously described.

A general illustrative scheme of the separation process described above is provided in FIG. 4.

The stream containing light olefins and paraffins (1), after being compressed in (K) and at least partially liquefied in (L), is fed to an absorption column (A) in which the olefins are absorbed by the absorbent solution (2) consisting of a hydrocarbon which is identical to the paraffin contained in a greater quantity in the starting mixture. A stream (3) containing hydrogen and/or inert products leaves the head of this column, and a stream (4) consisting of olefins, paraffins and the same paraffin absorbent, from the bottom, which is fed to the lower part of an extraction column (E). A liquid stream (6) essentially containing paraffins and the same paraffin absorbent, is obtained at the head, with the use of an extraction solvent (5) fed to the upper part of the extraction column (E), and a liquid stream (7) essentially containing the extracting solvent and olefins, from the bottom.

The bottom stream (7) is sent to a stripping column (S), from which olefins (8) are obtained at the head and the regenerated extracting solution (5) at the bottom, which is recycled to the extraction column (E).

The following three examples are provided for a better illustration of the invention but in no way limit its scope.

EXAMPLE 1

In a plant for the production of 500,000 t/year of ethylene, the product must be recovered from a stream of 13,625 kmoles/h of crude gas containing 17.1 mol. % of ethylene, 52.3% of ethane, 22.4% of hydrogen, 2.5% of CO, 3.1% of $CH_4$, 0.5% of propane and 2.2% of butane. With the proposed process schematized in FIG. 1, this stream, after being compressed at 31.4 bar, is put in contact, in a column operating at 40° C., with 148,000 kmol/h of a liquid stream, consisting of a 6M aqueous solution of $AgNO_3$ and 1M of $Fe(NO_3)_3$, to form an Ag-olefin salt complex which leaves the bottom of the column, whereas the gaseous stream without the olefin fraction (11,341 kmol/h with the following mol. % composition: ethylene 0.2, ethane 62.8, $H_2O$ 0.2, $H_2$ 26.9, CO 3, $CH_4$ 3.7, propane 0.6, butane 2.7) leaves the head. As the saline solution physically absorbs a portion of the paraffinic fraction and inert products, this solution, in order to increase the purity of the ethylene produced, is subjected to two successive expansions (at 15bar and 65° C. and at 7 bar and 90° C.), whose vapour phase is compressed to be sent to the absorption column, whereas the liquid phase is further depressurized to 0.9 bar before being sent to the regeneration column. The gaseous stream which leaves the head of this column has a flow-rate of 2,631 kmol/h and consists of ethylene with a very high purity (>99.99%) saturated with water. The regenerated saline solution leaves the bottom of the column and is sent, by means of a pump, to the head of the absorption column to restart its cycle; part of this solution, before reentering the cycle, is sent to a system into which air is insufflated, to re-oxidize the part of ferrous ions formed by the reducing action of hydrogen.

EXAMPLE 2

23.4 kmol/h of ethylene are to be recovered from a stream of 284.2 kmol/h having the following mol. % composition: ethylene 8.71, ethane 51.07, $H_2O$ 0.39, $N_2$ 0.23, CO 0.52, $CO_2$ 2.14, $CH_4$ 32.83, propane 1.27, propylene 2.84 using the process scheme described in FIG. 1. After eliminating the content of $C_2$, which in this case is an undesired compound in the stream of ethylene produced, with a caustic washing, the gas is compressed at 16 bar and then fed to the bottom of a column in which it comes into contact, in countercurrent, with a stream of 3,100 kmol/h of a 4M aqueous solution of $AgNO_3$. This column operates at 16 bar, 40° C. and a stream leaves its head, whose flow-rate is 248.3 kmol/h and mol. % composition: ethylene 0.55, ethane 58.46, $H_2$ 0.44, $N_2$ 0.27, CO 0.60, $CO_2$ 0.00, $CH_4$ 37.58, propane 1.46, propylene 0.18, $H_2O$ 0.46; the solution of $AgNO_3$ containing the Ag-olefin complex, leaves the bottom of the column and, after a first expansion at a pressure of 1.5 bar to remove the paraffins and inert products physically absorbed, which are then recompressed to be fed again to the absorption column, it is preheated to 90° C. and sent to the head of the regeneration column which operates at 0.7 bar. The gas leaving the head of the regenerator is cooled and compressed to eliminate the saturation water and is sent as product to the subsequent processing operations. Its quantity is 31.1 kmol/h and its mol. % composition: ethylene 75.14, ethane 24.47, $N_2$ 0.27, CO<0.01, $CH_4$ <0.01, propylene 0.18, $H_2O$ 0.16. The regenerated solution, after being cooled to 40° C., is pumped again to the head of the absorption column.

EXAMPLE 3

Figure 3:
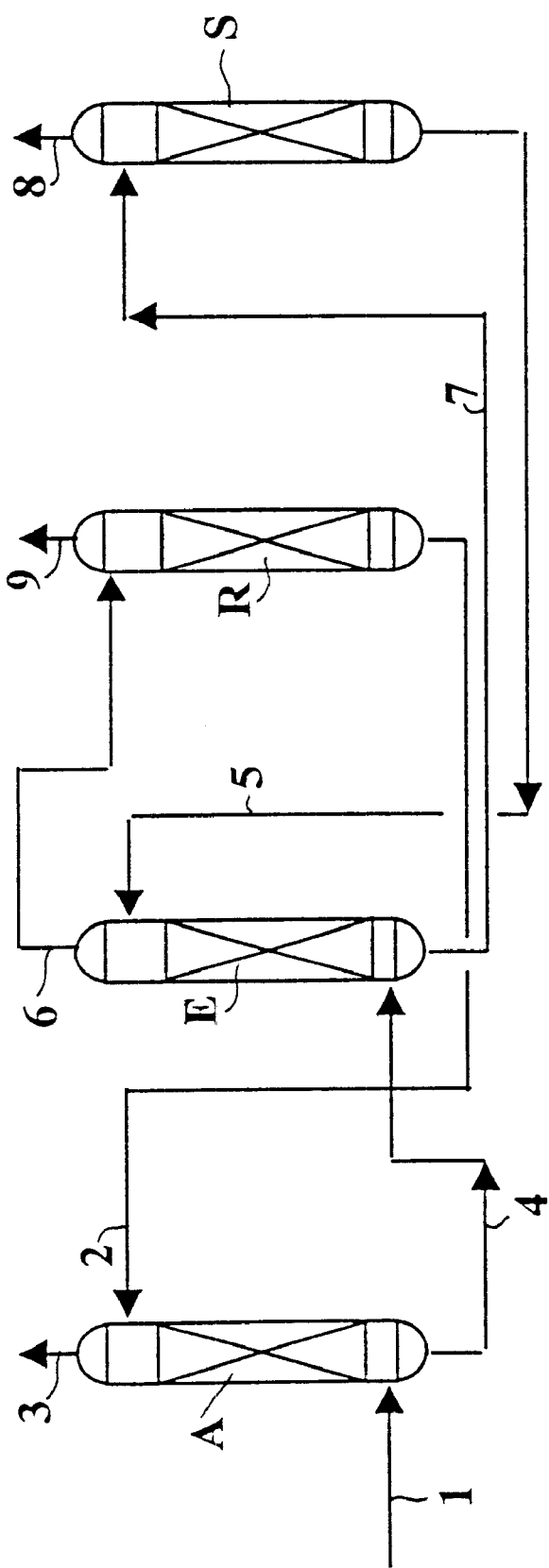

2,232 kmol/h of ethylene are to be recovered from a stream of 17,393 kmol/h of a gas having the following mol. % composition: ethane 40.54, $H_2$ 19.61, ethylene 13.08, $CH_4$ 25.65, propane 0.01, propylene 0.06, butane 0.01, butene 0.11, higher olefins 0.06, CO 0.87, using the process scheme of FIG. 3. This gas, after being compressed at 35 bar, is sent to the bottom of an absorption column in which it meets, in countercurrent, a stream of 7,640 $m^3$/h of "virgin naphtha". A gas essentially consisting of the fraction of inert gases contained in the charge, leaves the head of the column, more precisely the molar percentage composition of this gas is the following: ethane 1.67, $H_2$ 93.35, ethylene 0.56, $CH_4$ 2.19, CO 2.23. The stream of naphtha charged with olefinic and paraffinic hydrocarbons leaves the bottom, and is sent to the bottom of a liquid/liquid extraction column in which it is put in contact with 2,880 $m^3$/h of extracting liquid, consisting of a 6M aqueous solution of $AgNO_3$, fed to the head of the column. Two liquid phases leave the column, more precisely the extracting solution charged with olefins in the form of an Ag/olefin complex, leaves the bottom, whereas the naphtha charged with the paraffinic fraction alone, leaves the head. The extracting solution, after being depressurized at 0.7 bar, enters the head of the regeneration column from which the following products leave: from the head the product stream (2,271 kmol/h of gas with the following molar percentage composition: ethylene 98.28, propylene 0.47, butene 0.83, higher olefins 0.42); from the bottom the regenerated extracting solution which is sent, by means of a pump, to the head of the extraction column to restart the extraction cycle. The naphtha, charged with the paraffinic fraction alone, is, in turn, sent to a column which operates at a pressure that is slightly higher than atmospheric pressure (1.3 bar) in which the stripping takes place of the absorbed hydrocarbons, which leave the head (12,362 kmol/h of gas with the following composition: ethane 56.66, $H_2$ 6.76, ethylene 0.22, $CH_4$ 35.60, propane 0.02, butane 0.01, CO 0.72). The regenerated naphtha is then pumped to be sent to the head of the absorption column and subsequently restart the absorption cycle.

What is claimed is:

1. A process for the separation of light olefins from paraffins contained in mixtures containing hydrogen, comprising bringing said mixtures into contact with an aqueous solution of one or more silver compounds and one or more ferric compounds.

2. The process according to claim 1, wherein the silver compound is a salt.

3. The process according to claim 2, wherein the silver salt is silver nitrate.

4. The process according to claim 1, wherein the ferric compound is a salt.

5. The process according to claim 1, wherein the ferric salt is ferric nitrate.

6. The process according to claim 1, wherein in the aqueous solution, the silver compound is in a concentration ranging from 0.1 to 6 M and the ferric compound is in a concentration ranging from 0.1 to 4 M.

7. The process according to claim 6, wherein the silver compound is in a concentration ranging from 1 to 3 M and the ferric compound is in a concentration ranging from 0.5 to 2 M.

8. The process according to any of claims 1 to 7, comprising two steps:
    subjecting the mixture of light olefins and paraffins to absorption whereby the light olefins are absorbed by an absorbent consisting of the aqueous solution of one or more silver compounds and one or more ferric compounds, obtaining a stream containing paraffins and a stream containing the absorbent and light olefins absorbed;
    subjecting the stream containing the absorbent and light olefins absorbed to stripping whereby the light olefins absorbed are separated from the absorbent, which is recycled to the absorption step.

9. The process according to any of claims 1 to 7, comprising two steps:
    subjecting the mixture of light olefins and paraffins, after being at least partially liquefied, to an absorption in an absorption column, whereby the light olefins are absorbed by an absorbent consisting of the aqueous solution of one or more silver compounds and one or more ferric compounds, obtaining, at the head of the absorption column, a stream containing paraffins and inert products, which is sent to a subsequent fractionation step, and at the bottom of the absorption column, a stream containing the absorbent and light olefins absorbed;
    subjecting the stream containing the absorbent and light olefins absorbed to stripping, whereby the light olefins absorbed are separated from the absorbent, which is recycled to the absorption step.

10. A process for the separation of light olefins from paraffins contained in mixtures also containing hydrogen and/or other inert products which comprises the following steps:
    subjecting the mixture to a separation by absorption in a suitable hydrocarbon absorbent in order to separate the hydrogen and/or other inert products from the hydrocarbons contained therein;
    subjecting the mixture separated from the hydrogen and/or other inert products to a liquid/liquid extraction using a suitable extracting agent thereby obtaining a stream containing paraffins and the hydrocarbon absorbent and a stream containing the light olefins and extracting agent;
    subjecting the stream containing paraffins and hydrocarbon absorbent to regeneration in order to obtain a stream containing mainly said hydrocarbon absorbent, which is recycled to the separation step, and a stream containing mainly paraffins;
    subjecting the stream containing light olefins and the extracting agent to regeneration in order to obtain a stream containing mainly the extracting agent, which is recycled to the liquid-liquid extraction step, and a stream mainly containing light olefins.

11. The process according to any of claims 1 to 7, which comprises the following steps:

subjecting the mixture to separation by means of a hydrocarbon absorbent in order to separate the hydrogen from the hydrocarbons contained therein;

subjecting the mixture separated from the hydrogen to a liquid/liquid extraction using an extracting agent consisting of the aqueous solution of one or more silver compounds and one or more ferric compounds, thereby obtaining a stream containing light paraffins and the hydrocarbon absorbent and a stream containing light olefins and the extracting agent;

subjecting the stream containing paraffins and hydrocarbon absorbent to a regeneration to obtain a stream containing mainly the hydrocarbon absorbent, which is recycled to the separation step and a stream containing mainly paraffins;

subjecting the stream containing light olefins and the extracting agent to a regeneration to obtain a stream containing mainly the extracting agent, which is recycled to the extraction step and a stream containing mainly paraffins;

subjecting the stream containing light olefins and the extracting agent to a regeneration to obtain a stream containing mainly the extracting agent, which is recycled to the extraction step and a stream containing mainly light olefins.

12. A process for the separation of light olefins from paraffins contained in mixtures also containing hydrogen and/or other inert products, which comprises the following steps:

subjecting the mixture of light olefins and paraffins, after being at least partially liquefied, to an absorption in an absorption column by means of a paraffin absorbent identical to the paraffins contained in the mixture and in a greater quantity than said paraffins, thereby obtaining, at the head of the absorption column, inert products and/or hydrogen and, at the bottom of the absorption column, a stream containing olefins and paraffins also comprising the paraffin absorbent;

subjecting the bottom stream to a liquid-liquid extraction in an extraction column using a suitable extracting agent, obtaining at the head of the extraction column, a stream mainly containing paraffins comprising the paraffin absorbent and, at the bottom of the extraction column, a stream mainly containing olefins and the extracting agent;

subjecting the stream containing olefins and the extracting agent to stripping whereby the olefins are separated from the extracting agent, which is recycled to the liquid-liquid extraction step.

13. The process for the separation of light olefins according to any of claims 1 to 7, which comprises the following steps:

subjecting the mixture of light olefins and paraffins, after being at least partially liquefied, to an absorption in an absorption column by means of a paraffin absorbent identical to the paraffins contained in the mixture and in a greater quantity than said paraffins, thereby obtaining, at the head of the absorption column, inert products and/or hydrogen and, at the bottom of the absorption column, a stream containing olefins and paraffins also comprising the paraffin absorbent;

subjecting the bottom stream to a liquid-liquid extraction in an extraction column using an extracting agent consisting of the aqueous solution of one or more silver compounds and one or more ferric compounds, obtaining at the head of the extraction column, a stream mainly containing paraffins and, at the bottom of the extraction column, a stream mainly containing olefins and the extracting agent;

subjecting the stream containing olefins and the extracting agent to stripping whereby the olefins are separated from the extracting agent, which is recycled to the liquid-liquid extraction step.

* * * * *